US009051227B2

(12) United States Patent
Roy et al.

(10) Patent No.: US 9,051,227 B2
(45) Date of Patent: *Jun. 9, 2015

(54) IN-SITU METHOD FOR PREPARING HYDROLYZED ACYL HALIDE COMPOUND

(71) Applicant: Dow Global Technologies LLC, Midland, MI (US)

(72) Inventors: Abhishek Roy, Edina, MN (US); Steven D. Jons, Eden Prairie, MN (US); Joseph D. Koob, Jordan, MN (US); Martin H. Peery, Bloomington, MN (US); XiaoHua Sam Qiu, Midland, MI (US); Steven Rosenberg, Shorewood, MN (US); Ian A. Tomlinson, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 183 days.

This patent is subject to a terminal disclaimer.

(21) Appl. No.: 13/844,840

(22) Filed: Mar. 16, 2013

(65) Prior Publication Data
US 2014/0264161 A1 Sep. 18, 2014

(51) Int. Cl.
C07B 41/08 (2006.01)
C08G 69/26 (2006.01)
C08G 69/00 (2006.01)

(52) U.S. Cl.
CPC ............... *C07B 41/08* (2013.01); *C08G 69/26* (2013.01); *C08G 69/00* (2013.01)

(58) Field of Classification Search
None
See application file for complete search history.

(56) References Cited

U.S. PATENT DOCUMENTS

| | | |
|---|---|---|
| 3,304,310 A | 2/1967 | Hari et al. |
| 3,686,116 A | 8/1972 | Rio |
| 3,878,109 A | 4/1975 | Ikeda et al. |
| 4,259,183 A | 3/1981 | Cadotte |
| 4,265,745 A | 5/1981 | Kawaguchi et al. |
| 4,277,344 A | 7/1981 | Cadotte |
| 4,529,646 A | 7/1985 | Sundet |
| 4,606,943 A | 8/1986 | Rak et al. |
| 4,626,468 A | 12/1986 | Sundet |
| 4,643,829 A | 2/1987 | Sundet |
| 4,719,062 A | 1/1988 | Sundet |
| 4,758,343 A | 7/1988 | Sasaki et al. |
| 4,761,234 A | 8/1988 | Uemura et al. |
| 4,783,346 A | 11/1988 | Sundet |
| 4,812,270 A | 3/1989 | Cadotte et al. |
| 4,830,885 A | 5/1989 | Tran et al. |
| 4,888,116 A | 12/1989 | Cadotte et al. |
| 4,948,507 A | 8/1990 | Tomaschke |
| 4,950,404 A | 8/1990 | Chau |
| 4,960,517 A | 10/1990 | Cadotte |
| 5,015,380 A | 5/1991 | Sundet |
| 5,015,382 A | 5/1991 | Sundet |
| 5,019,264 A | 5/1991 | Arthur |
| 5,051,178 A | 9/1991 | Uemura et al. |
| 5,160,619 A | 11/1992 | Yamaguchi et al. |
| 5,246,587 A | 9/1993 | Tomaschke |
| 5,254,261 A | 10/1993 | Tomaschke et al. |
| 5,290,452 A | 3/1994 | Schucker |
| 5,336,409 A | 8/1994 | Hachisuka et al. |
| 5,576,057 A | 11/1996 | Hirose et al. |
| 5,582,725 A | 12/1996 | McCray et al. |
| 5,593,588 A | 1/1997 | Kim et al. |
| 5,614,099 A | 3/1997 | Hirose et al. |
| 5,616,249 A | 4/1997 | Hodgdon |
| 5,693,227 A | 12/1997 | Costa |
| 5,733,602 A | 3/1998 | Hirose et al. |
| 5,736,371 A | 4/1998 | Samain et al. |
| 5,744,039 A | 4/1998 | Itoh et al. |
| 5,783,079 A | 7/1998 | Kumano et al. |
| 5,843,351 A | 12/1998 | Hirose et al. |
| 5,876,602 A | 3/1999 | Jons et al. |
| 5,989,426 A | 11/1999 | Hirose et al. |
| 6,024,873 A | 2/2000 | Hirose et al. |
| 6,086,764 A | 7/2000 | Linder et al. |
| 6,162,358 A | 12/2000 | Li et al. |
| 6,280,853 B1 | 8/2001 | Mickols |
| 6,337,018 B1 | 1/2002 | Mickols |
| 6,406,626 B1 | 6/2002 | Murakami et al. |
| 6,464,873 B1 | 10/2002 | Tomaschke |
| 6,521,130 B1 | 2/2003 | Kono et al. |
| 6,562,266 B2 | 5/2003 | Mickols |
| 6,723,241 B2 | 4/2004 | Mickols |
| 6,723,422 B1 | 4/2004 | Hirose et al. |
| 6,878,278 B2 | 4/2005 | Mickols |
| 7,279,097 B2 | 10/2007 | Tomioka et al. |

(Continued)

FOREIGN PATENT DOCUMENTS

| | | |
|---|---|---|
| DE | 2530562 | 1/1977 |
| EP | 0302149 | 2/1989 |
| JP | 53146275 | 12/1978 |
| WO | 2009129354 | 10/2009 |
| WO | 2010042250 | 4/2010 |
| WO | 2010120326 | 10/2010 |
| WO | 2010120327 | 10/2010 |
| WO | 2011105278 | 9/2011 |
| WO | 2012020680 | 2/2012 |
| WO | 2012090862 | 7/2012 |
| WO | 2012102942 | 8/2012 |
| WO | 2012102943 | 8/2012 |
| WO | 2012102944 | 8/2012 |
| WO | 2013032586 | 3/2013 |
| WO | 2013048762 | 4/2013 |
| WO | 2013048763 | 4/2013 |
| WO | 2013048764 | 4/2013 |
| WO | 2013048765 | 4/2013 |

OTHER PUBLICATIONS

Marvel, et al., Journal of Organic Chemistry, vol. 18, No. 12, (1953) 1664-1669.

(Continued)

*Primary Examiner* — Joseph D Anthony
(74) *Attorney, Agent, or Firm* — Edward W. Black

(57) ABSTRACT

An in-situ method for preparing a hydrolyzed, acyl halide-containing compound by combining a reactant including a plurality of acyl halide functional groups containing reactant, a tri-hydrocarbyl phosphate compound and water within a hydrocarbon or halogenated hydrocarbon solvent.

14 Claims, No Drawings

(56) References Cited

U.S. PATENT DOCUMENTS

| | | |
|---|---|---|
| 7,806,275 B2 | 10/2010 | Murphy et al. |
| 7,815,987 B2 | 10/2010 | Mickols et al. |
| 7,882,963 B2 | 2/2011 | Mickols et al. |
| 7,905,361 B2 | 3/2011 | Niu et al. |
| 7,918,349 B2 | 4/2011 | Mickols et al. |
| 8,177,978 B2 | 5/2012 | Kurth et al. |
| 2008/0185332 A1 | 8/2008 | Niu et al. |
| 2009/0071903 A1 | 3/2009 | Nakatsuji et al. |
| 2009/0107922 A1 | 4/2009 | Zhang et al. |
| 2009/0220690 A1 | 9/2009 | Niu et al. |
| 2009/0272692 A1 | 11/2009 | Kurth et al. |
| 2010/0062156 A1 | 3/2010 | Kurth et al. |
| 2011/0005997 A1 | 1/2011 | Kurth et al. |
| 2011/0049055 A1 | 3/2011 | Wang et al. |
| 2011/0220569 A1 | 9/2011 | Mickols et al. |
| 2012/0248027 A1 | 10/2012 | Sasaki et al. |
| 2012/0261332 A1 | 10/2012 | Takagi et al. |
| 2012/0261344 A1 | 10/2012 | Kurth et al. |
| 2014/0206900 A1* | 7/2014 | Qiu et al. .................. 562/495 |
| 2014/0264161 A1* | 9/2014 | Roy et al. ................ 252/182.15 |
| 2014/0272134 A1* | 9/2014 | Roy et al. .................... 427/244 |

OTHER PUBLICATIONS

Dow Global Technologies LLC, PCT/US13/020072, filed Jan. 3, 2013.

* cited by examiner

IN-SITU METHOD FOR PREPARING HYDROLYZED ACYL HALIDE COMPOUND

FIELD OF THE INVENTION

The present invention is directed toward in-situ methods for preparing a variety of hydrolyzed acyl halide compounds in a hydrocarbon or halogenated hydrocarbon solution.

BACKGROUND

While acyl halide compounds such as benzene-1,3,5-tricarboyl trichloride and adipoyl dichloride are readily soluble in a variety of hydrocarbon and halogenated hydrocarbon solvents, their hydrolyzed and partially hydrolyzed analogs (3,5-bis(chlorocarbonyl)benzoic acid and 6-chloro-6-oxohexanoic acid) are only slightly soluble, e.g. less than 0.02 wt. %. As a consequence, it is difficult to prepare in-situ solutions of such hydrolyzed reaction products in a hydrocarbon or halogenated hydrocarbon solvent. Nevertheless, hydrocarbon and halogenated hydrocarbon solutions including such hydrolyzed reaction products would be useful in a variety of applications including the preparation of polyamides. U.S. Pat. No. 5,736,371 describes a process for preparing succinic acid monochloride. Marvel, et al., Journal of Organic Chemistry, vol 18, no. 12, (1953) 1664-1669 describes a process for preparing p-chloroformylbenzoic acid.

BRIEF SUMMARY OF THE INVENTION

The present invention includes a method for preparing a reaction product comprising at least one acyl halide functional group and a carboxylic acid functional group in a solution comprising a hydrocarbon or halogenated hydrocarbon solvent, wherein the reaction product has a solubility limit of less than 1 weight percent in the solvent and is produced to a molar concentration greater than its solubility limit within the solvent while remaining soluble in solution. The solution comprises at least 80 v/v % of the solvent in combination with: i) water at a molar concentration greater than its solubility limit within the solvent but less that its solubility limit with the solution, ii) a reactant comprising a plurality of acyl halide functional groups at a molar concentration less than its solubility limit within the solvent and at a molar ratio with water from 1:2 to 1000:1, and iii) a tri-hydrocarbyl phosphate compound at a molar ratio with the hydrocarbon reactant from 100:1 to 1:1000.

While many different embodiments are described, preferred embodiments provide a method for preparing a hydrolyzed or partially hydrolyzed acyl halide compound at a concentration above its solubility limit within the corresponding hydrocarbon or halogenated hydrocarbon solvent.

DETAILED DESCRIPTION OF THE INVENTION

The present invention broadly includes in-situ methods for preparing reaction products in a solution comprising: a reactant, hydrocarbon or halogenated hydrocarbon solvent, water (preferably deionized) and a tri-hydrocarbyl phosphate compound.

The reactant(s) of the present invention includes an aliphatic or arene moiety including a plurality of acyl halide functional groups. The reaction product comprises a hydrolyzed, preferably mono-hydrolyzed, analog of the reactant.

In a preferred set of embodiments, the reactant and reaction product have molecular weights less than 700, 600, 500, 400 or 300 atomic mass units, "amu" (Daltons). In another set of embodiments, the reactant and reaction product comprises equal to or less than 30, 20, 15 or 12 carbon atoms, and preferably include more than 3 carbon atoms. In yet another set of embodiments, the reactant and reaction product comprises from 4 to 12 carbon atoms. Non-limiting examples of reactants based upon aliphatic moieties include: $C_4$ through $C_{12}$ alkanes (e.g. succinyl, glutaroyl, adipoyl, heptanedioyl, octanedioyl, nonanedioyl, decanedioyl, undecanedioyl and dodecanedioyl di and tri chloride), cycloalkanes (e.g. cyclopropane tri carboxylic acid chloride, cyclobutane tetra carboxylic acid chloride, cyclopentane tri carboxylic acid chloride, cyclopentane tetra carboxylic acid chloride, cyclohexane tri carboxylic acid chloride, tetrahydrofuran tetra carboxylic acid chloride, cyclopentane dicarboxylic acid chloride, cyclobutane dicarboxylic acid chloride, cyclohexane di carboxylic acid chloride, tetrahydrofuran dicarboxylic acid chloride, cyclohexane dichloride, cyclohexane-1,3,5-tricarbonyl trichloride, and decahydronaphthalene-2,6-dicarbonyl dichloride. Non-limiting examples of reactants based upon arene moieties include: terephthaloyl dichloride, isophthalic acid chloride, benzene-1,3,5-tricarbonyl trichloride and naphthalene-2,6-dicarbonyl dichloride. Additional examples of reactants include branched analogs of the preceding compounds along analogs including additional acyl halide functional groups. Examples of preferred reaction products include the mono-hydrolyzed analog of the preceding compounds.

The selection of hydrocarbon or halogenated hydrocarbon solvent is not particularly limited and combinations of multiple solvents may be used. The solvent is preferably a liquid at 20° C. (101 kPa). The solvent preferably has a water solubility of less than 800 ppm (and more preferably less than 500, 400, 300, or 200, or in some embodiments, less than 150 ppm). As used herein, the term "water solubility" refers to the concentration of water that is soluble in a chosen hydrocarbon solvent measured at 20° C. (101 kPa) as measured by ASTM D4928-11. Non-limiting examples of applicable hydrocarbon solvents include: paraffins (e.g. hexane, cyclohexane, heptane, octane, dodecane), isoparaffins (e.g. ISOPAR™ L), aromatics (e.g. benzene, 1,3,5-trimethylbenzene, toluene) and halogenated hydrocarbons (e.g. FREON™ series, chlorobenzene, di and trichlorobenzene).

Tri-hydrocarbyl phosphate compounds applicable in the present invention include those represented by Formula (I):

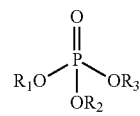

Formula (I)

wherein "P" is phosphorous, "O" is oxygen and $R_1$, $R_2$ and $R_3$ are independently selected from hydrogen and hydrocarbyl groups comprising from 1 to 10 carbon atoms, with the proviso that no more than one of $R_1$, $R_2$ and $R_3$ are hydrogen. $R_1$, $R_2$ and $R_3$ are preferably independently selected from aliphatic and arene groups. Applicable aliphatic groups include both branched and unbranched species, e.g. methyl, ethyl, propyl, isopropyl, butyl, isobutyl, pentyl, 2-pentyl, 3-pentyl, cyclopentyl, cyclohexyl, etc.; however, alkyl groups having from 3 to 10 carbon atoms are preferred. Applicable arene groups include phenyl and naphthyl groups. Specific examples of tri-hydrocarbyl phosphate compounds include: tripropyl phosphate, tributyl phosphate, tripentyl phosphate, trihexyl phosphate, triphenyl phosphate, propyl biphenyl phosphate, dibutyl phenyl phosphate, butyl diethyl phosphate, dibutyl hydrogen phosphate, butyl heptyl hydrogen phosphate and butyl heptyl hexyl phosphate.

The aforementioned constituents are combined to form a solution comprising at least 80 v/v % solvent, and in some embodiments at least 90 v/v %, 92 v/v % or 95 v/v % solvent along with: i) water at a molar concentration greater than its solubility limit (i.e. miscibility limit) within the solvent but less that its solubility limit with the solution, ii) the reactant at a molar concentration less than its solubility limit within the solvent and at a molar ratio with water from 1:2 to 1000:1, and iii) the tri-hydrocarbyl phosphate compound at a molar ratio with the hydrocarbon reactant from 100:1 to 1:1000. In a preferred embodiment, the solution comprises the tri-hydrocarbyl phosphate compound at a molar ratio with the reactant from 10:1 to 1:100. In another embodiment, the solution comprises the reactant at a molar ratio with water of from 1:2 to 200:1, and in other embodiments from 1:2 to 100:1. In still another embodiment, the solution includes at least one but preferably all of the following: water at a concentration of less than 1 wt %, the reactant at a concentration of less than 10 wt % or the tri-hydrocarbyl phosphate compound at a concentration of less than 10 wt %. In yet other set of embodiments, the solution includes at least one but preferably all of the following: water at a concentration of less than 0.5 wt %, the reactant at a concentration of less than 5 wt %, or the tri-hydrocarbyl phosphate compound at a concentration of less than 5 wt %.

The aforementioned constituents may be combined and mixed within a reaction vessel at room temperature. While the order of addition is not particularly limited, in preferred embodiments the reactant is contacted with the tri-hydrocarbyl phosphate compound prior to contact with water. The resulting reaction product is the hydrolyzed analog of the reactant. In preferred embodiments, the mono-hydrolyzed analog of the reactant is the dominant reaction product, e.g. preferably at least 60 wt. %, at least 70 wt. %, at least 80 wt. % or still more preferably at least 90 wt %. Representative reaction pathways are illustrated below.

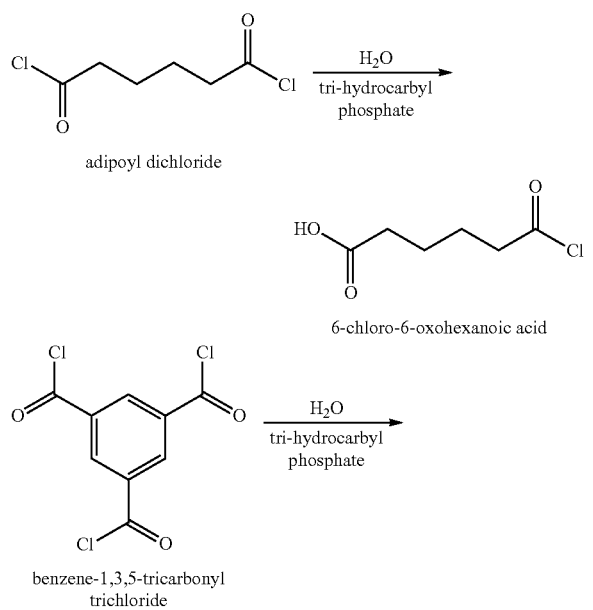

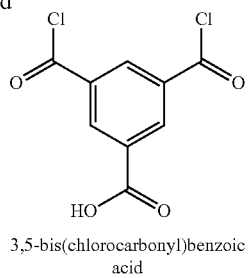

3,5-bis(chlorocarbonyl)benzoic acid

The reaction product has a solubility limit of less than 1 wt. % in the solvent, and in some embodiments less than 0.1 wt %, 0.05 wt % and still others less than even 0.02 wt %. While the reaction product is produced to a molar concentration greater than its solubility limit (e.g. greater than 10%) within the solvent, the product remains soluble in solution. While not wishing to be bound by theory, it is believed that the subject class of tri-hydrocarbyl phosphates increases the solubility of water (and hydrolyzed reaction product) within the hydrocarbon solvent and facilitates hydrolysis of the reactant. Surprisingly, the reaction product is highly selective toward the mono-hydrolyzed form. Hydrocarbon-based solutions including relatively higher concentrations of the hydrolyzed reaction product are useful in a variety of applications. In one application, solutions including both the reactant and hydrolyzed product (particularly mono-hydrolyzed product) are useful in coating applications to prepare polyamides.

Many embodiments of the invention have been described and in some instances certain embodiments, selections, ranges, constituents, or other features have been characterized as being "preferred." Characterizations of "preferred" features should in no way be interpreted as deeming such features as being required, essential or critical to the invention. For purposes of this description, the terms "acyl halide" and "acid halide" have the same meaning. While much of the description has focused upon acyl chlorides, non-chloride halides are also included. The term "solubility limit" refers to the point at which no additional amount of a constituent, (e.g. water, reaction product, reactant) is miscible or dissolvable with the hydrocarbon solvent or solution, as measured at 20° C. and 101 kPa. Unless otherwise stated, all solubility related parameters are determined at 20° C. and 101 kPa.

Examples

In Situ Preparation of Mono-Hydrolyzed Polyfunctional Acid Chlorides

A solution of trialkylphosphate in a hydrocarbon solvent was combined with trace water and stirred vigorously at room temperature (reactant concentrations are provided in Table 1 below). The reaction was monitored by proton NMR. Over time the water is consumed and the composition of product reaction mixture becomes constant. If the desired amount of hydrolysis was not obtained, a second addition of water was introduced to the reaction mixture (noted as a "+" quantity in the water concentration column in Table 1). The solution was allowed to stir until the product reaction mixture remained constant as observed by $^1$H NMR and the final product reaction mixture is noted in Table 1.

TABLE 1

| Ex. No. | Acid Chloride[1] type | Acid Chloride[1] conc. (wt %) | Trialkylphosphate[2] type | Trialkylphosphate[2] conc. (wt %) | water conc. (ppm) | solvent | reaction time (min) | product reaction mixture (mole acid chloride:mole mono-hydrolyzed acid chloride) |
|---|---|---|---|---|---|---|---|---|
| 1-1 | TMC | 0.29 | TBP | 1.1 | 99 | Isopar L | 10 | 59:41 |
| 1-2 | IPC | 1.8 | TBP | 0.47 | 50 + 100 | Isopar L | 1200 | 88:12 |
| 1-3 | NO2IPC | 0.26 | TBP | 0.29 | 50 | Isopar L | 400 | 80:20 |
| 1-4 | TMC | 2.3 | TBP | 1.0 | 50 + 200 | 90 Isopar L: 10 toluene | 120 | 70:30 |
| 1-5 | TMC | 0.3 | TEP | 1.0 | 99 | Isopar L | 5 | 85:15 |
| 1-6 | TMC | 0.32 | TEHP | 1.0 | 99 | Isopar L | 60 | 69:31 |

[1]trimesoyl chloride (TMC); isophthaloyl chloride (IPC); 5-nitroisophthaloyl chloride (NO2IPC)
[2]tributylphosphate (TBP); triethylphosphate (TEP); triethylhexylphophate (TEHP)

The invention claimed is:

1. A method for preparing a reaction product comprising at least one acyl halide functional group and a carboxylic acid functional group in a solution comprising a hydrocarbon or halogenated hydrocarbon solvent having a water solubility of less than 800 ppm;
   wherein the reaction product has a solubility limit of less than 1 weight percent in the solvent and is produced to a molar concentration greater than its solubility limit within the solvent while remaining soluble in solution, and
   wherein the solution comprises at least 80 v/v % solvent in combination with:
   i) water at a molar concentration greater than its solubility limit within the solvent but less that its solubility limit with the solution,
   ii) a reactant comprising a plurality of acyl halide functional groups at a molar concentration less than its solubility limit within the solvent and at a molar ratio with water from 1:2 to 1000:1, and
   iii) a tri-hydrocarbyl phosphate compound at a molar ratio with the reactant from 100:1 to 1:1000 wherein the tri-hydrocarbyl compound is represented by:

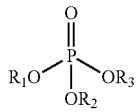

wherein $R_1$, $R_2$ and $R_3$ are independently selected from hydrogen and hydrocarbyl groups comprising from 1 to 10 carbon atoms, with the proviso that no more than one of $R_1$, $R_2$ and $R_3$ are hydrogen.

2. The method of claim 1 wherein the reactant and reaction product both have a molecule weight less than 700 amu (Daltons).

3. The method of claim 1 wherein the reactant and reaction product both have a molecule weight less than 300 amu (Daltons).

4. The method of claim 1 wherein the reactant and reaction product both comprise equal to or less than 30 carbon atoms.

5. The method of claim 1 wherein the reactant and reaction product both comprise from 4 to 12 carbon atoms.

6. The method of claim 1 wherein the reactant comprises a carbon containing moiety selected from: an aliphatic or arene group substituted with a plurality of acyl halide functional groups; and the reaction product comprises an aliphatic or arene group substituted with at least one acyl halide functional group and a carboxylic acid functional group.

7. The method of claim 1 wherein the reaction product comprises an aliphatic or arene group substituted with at least one acyl halide functional group and single carboxylic acid functional group.

8. The method of claim 1 wherein the solution comprises:
   i) water at a concentration of less than 1 wt. %,
   ii) the reactant at a concentration of less than 10 wt. % and
   iii) the tri-hydrocarbyl phosphate compound at a concentration of less than 10 wt. %.

9. The method of claim 1 wherein the solution comprises:
   i) water at a concentration of less than 0.5 wt. %,
   ii) the reactant at a concentration of less than 5 wt. %, and
   iii) the tri-hydrocarbyl phosphate compound at a concentration of less than 5 wt. %.

10. The method of claim 1 wherein the solution comprises the reactant at a molar ratio with water from 1:2 to 100:1.

11. The method of claim 1 wherein the solution comprises the tri-hydrocarbyl phosphate compound at a molar ratio with the reactant of 10:1 to 1:100.

12. The method of claim 1 wherein the hydrocarbon solvent has a water solubility of less than 150 ppm.

13. The method of claim 1 wherein $R_1$, $R_2$ and $R_3$ are independently selected from: aliphatic and arene groups.

14. The method of claim 1 wherein $R_1$, $R_2$ and $R_3$ are independently selected from alkyl groups.

* * * * *